United States Patent [19]

Chubbuck

[11] 4,026,276
[45] May 31, 1977

[54] INTRACRANIAL PRESSURE MONITOR

[75] Inventor: John G. Chubbuck, Silver Spring, Md.

[73] Assignee: The Johns Hopkins University, Baltimore, Md.

[22] Filed: Apr. 5, 1976

[21] Appl. No.: 673,970

[52] U.S. Cl. .............................. 128/2 P; 128/2.1 R; 128/2.05 E; 73/398 C
[51] Int. Cl.² ........................................ A61B 5/02
[58] Field of Search ............... 128/2 P, 2 R, 2.1 A, 128/2.05 E, 2.05 D; 73/398 R, 398 C, 399

[56] References Cited

UNITED STATES PATENTS

| 3,504,664 | 4/1970 | Haddad | 128/2.1 R |
| 3,738,356 | 6/1973 | Workman | 73/398 R X |
| 3,853,117 | 12/1974 | Murr | 128/2 P X |
| 3,943,915 | 3/1976 | Severson | 128/2 P |
| 3,958,558 | 5/1976 | Dunphy et al. | 128/2 P |
| 3,977,391 | 8/1976 | Fleischmann | 128/2.05 E X |

Primary Examiner—Stephen C. Pellegrino
Attorney, Agent, or Firm—Robert E. Archibald; Kenneth E. Darnell

[57] ABSTRACT

Pressure monitoring apparatus implantable in the cranium to measure intracranial pressure, the apparatus comprises a passive resonant circuit having a natural frequency influenced by ambient pressure. The resonant circuit has inductance and capacitance capability for comparing the local environmental pressure to that of a volume of gas trapped inside the apparatus, the environmental pressure being measured by observation of the frequency at which energy is absorbed from an imposed magnetic field located externally of the cranium.

35 Claims, 18 Drawing Figures

4,026,276

INTRACRANIAL PRESSURE MONITOR

STATEMENT OF GOVERNMENT INTEREST

The invention described herein was made in the course of work under a grant or award from the Department of Health, Education, and Welfare.

BACKGROUND OF THE INVENTION

A. Field of the Invention

The invention finds utility for monitoring intracranial pressure in diagnostic and post-operative situations, the pressure-sensitive apparatus of the invention being totally implantable in the cranium.

B. Description of the Prior Art

The need for monitoring intracranial pressure has long been recognized for applications involving intracranial hypertension. Although such a need is well-identified for hydrocephalic individuals and individuals who have undergone neurosurgery, other critical situations involve individuals subject to brain swelling, edema, obstruction of cerebral spinal fluid pathways, or intracranial space-occupying lesions. Accurate monitoring of the intracranial pressure in certain of these situations allows institution of emergency procedures should pressure rise to dangerous levels.

Common methods for measuring intracranial pressure involve implantation of a pressure transducer having wires which pass through the skull and scalp. Measurement of the pressure of the cerebral spinal fluid, which can be related to the intracranial pressure, has generally involved lumbar puncture or introduction of a catheter into the ventricular spaces. None of these techniques are suitable for prolonged measurement of these pressures. Danger of infection, patient discomfort, and the certain need for a second operation to remove the measuring device are negative aspects of all of these prior art techniques. Certain of these techniques actually cause leakage and blockage of the hydraulic system within the cranium and directly affect pressure measurements.

A number of intracranial pressure measurement systems have been postulated and even tested in recent years. Virtually all of these systems involved placement of a transducer within the cranium with wires passing through the scalp to a recordation sub-system. Use of these systems posed a constant risk of infection and required constant adjustments to compensate for changes in the position of the patient. Such systems were necessarily short-term in use. Attempts were made by Atkinson et al and Olson et al. in 1967 and 1968 respectively to implant a variable capacitor mounted on two sides of an air-filled tambour, the resonant frequency of the variable tuned circuit then being read by imposing a radio wave thereon through the intact scalp. The devices thus proposed were subject to extreme fragility and needed to be constantly recalibrated for temperature and atmospheric pressure changes. Further, error was prevalent in the use of these devices due to drift in the zero reading, i. e., "baseline drift".

SUMMARY OF THE INVENTION

The invention is a system for monitoring either continuously or intermittently the intracranial pressure, the uses of which have been described hereinabove. In particular, the invention provides a passive implantable pressure transducer useful in association with external interrogation and recordation apparatus for determining intracranial pressure. The present implantable pressure transducer can be permanently placed in a trephine or "burr"hole in the skull and operates without the need for percutaneous extracranial connections to monitoring apparatus.

Measurement of intracranial pressure gradients are necessary to anticipate and thereby effectively treat secondary complications of cerebral insults, such as transtentorial herniations, obstructuve hydrocephalus, and rapidly expanding hematomas. The present invention allows ready determination of specific treatment modalities to reverse these complications as well as providing useful information in the treatment of cerebral edema of idiopathic hydrocephalus in children. Since individuals in whom intracranial pressure monitoring is most desirable are those in whom neurosurgical intervention is necessary or anticipated, the unavoidable requirement for a small burr hole through the skull is acceptable. However, unlike previously used devices, the present pressure transducer is operable without the need for electrical circuits or manometric conduits which extend through the scalp, both of which offer a portal of entry for infection and compromise patient mobility.

The implantable pressure transducer hereby provided comprises a non-porous yet complaint enclosure which contains a specific mass of trapped gas and a passive r-f resonant circuit (inductance and capacitance) having a natural frequency which is influenced by the pressure of the environment of the transducer. The capacitance portion of the r-f resonant circuit is comprised of two bellows each with one closed end. The closed ends, lying in close proximity to each other, form a capacitance directly proportional to their areas and inversely proportional to their spacing. Increasing intracranial pressure elongates both bellows diminishing the spacing of the closed ends and, thereby, lowering the natural frequency of the resonant circuit. An equivalent embodiment of this principal is achieved with one bellows having its closed end lying in close proximity to a fixed conductive surface. In effect, the transducer acts to compare the surrounding environmental pressure to that of the gas trapped inside the transducer.

The resonant frequency of the transducer is sensed by monitoring apparatus external of the cranium by determining the natural frequency at which the transducer absorbs energy from an electromagnetic field. This measured frequency is then converted directly to a pressure reading.

The implantable transducer is characterized by the following features:

1. sufficient elastic compliance so that measurable deformations result from small changes in intracranial pressure;

2. non-porosity of the enclosure so that the mass of gas trapped within the device does not change meaningfully during the useful life of the device; and, 3 electrical non-conductivity so that the resonant circuit in the device is not shielded from an external monitoring radio-frequency magnetic field.

These characteristics are produced primarily by utilization of a combination of ceramic (non-porous and non-conductive) and metallic (non-porous and compliant) material to form the chamber enclosing the trapped volume of gas within the device.

In addition to other "absolute pressure" embodiments of the invention, a "gauge pressure" embodiment of the invention is also provided in which the difference in pressure between the intracranial pressure and the pressure immediately beneath the scalp, which pressure is an approximation of barometric pressure, is measured.

Accordingly, it is a primary object of the invention to provide a system for monitoring intracranial pressure without the need for percutaneous extracranial electrical connections or manometric conduits.

It is a further object of the invention to provide an implantable pressure transducer which passively provides an indication of intracranial pressure to extracranial monitoring apparatus on interrogation of the transducer.

It is yet another object of the invention to provide an implantable pressure transducer having sufficient elastic compliance to be measurably deformed by changing intracranial pressure while being sufficiently non-porous to prevent loss of entrapped gas from the transducer or leakage of body fluids into the transducer.

It is yet another object of the invention to provide am implantable pressure transducer which provides a measure of the difference between the intracranial pressure and the pressure immediately beneath the scalp, which pressure is an approximation of atmospheric, and thus barometric, pressure.

Further objects and advantages of the invention will become more readily apparent in light of the following detailed description of the preferred embodiments of the invention.

DESCRIPTION OF THE PREFERRED EMBODIMENTS

The invention particularly provides an intracranial pressure sensing implant, referred to hereinafter as the transducer, which contains a passive radio-frequency resonant circuit having a natural frequency influenced by the pressure of the transducer's environment. The transducer is configured so that a comparison is continuously made between the environmental pressure and the pressure of a fixed mass of gas entrapped inside the transducer. The environmental pressure is effectively measured by observing the frequency at which the transducer absorbs energy from an externally imposed electromagnetic field. The invention further provides apparatus for imposing an electromagnetic field on the transducer and for remotely measuring the frequency at which energy is absorbed by the transducer.

Figure 1:
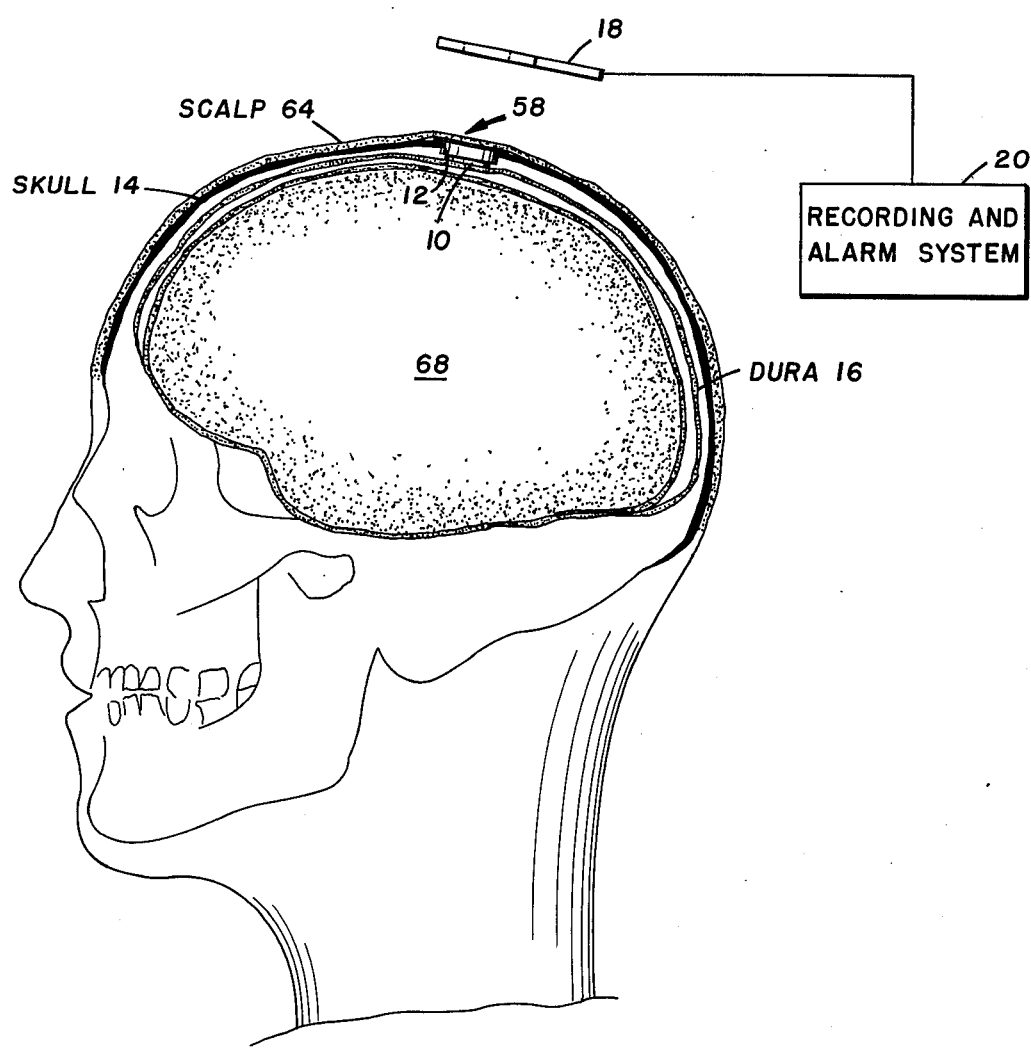
FIG. 1 is a schematic illustrating the environment and general operation of the invention.
Figure 4:
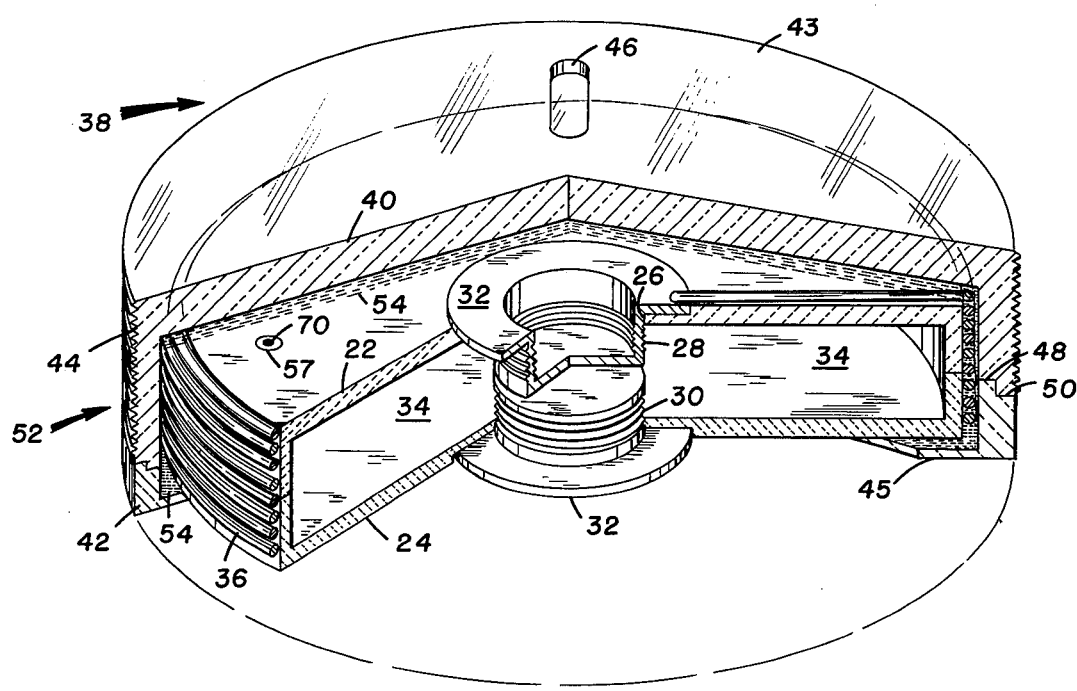
FIG. 4 is a perspective in partial section of one embodiment of the implantable pressure transducer.
Figure 2:
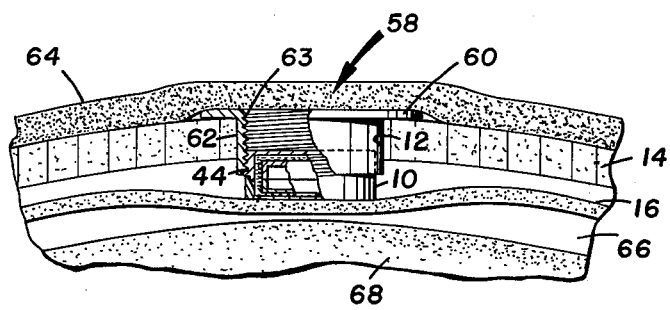
FIG. 2 is a detailed elevation in partial section of an implanted transducer according to one embodiment of the invention.
Figure 3A:
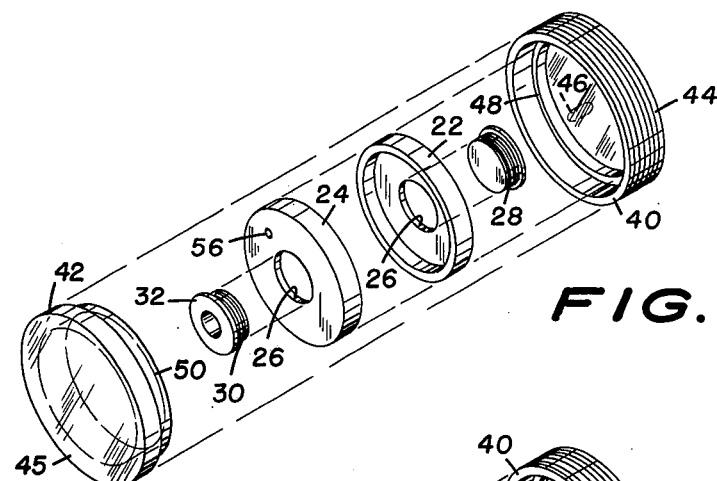
FIGS. 3a, 3b, and 3d are assembly views in perspective illustrating the several parts of one embodiment of the implantable pressure transducer in various stages of assembly.
Figure 3B:
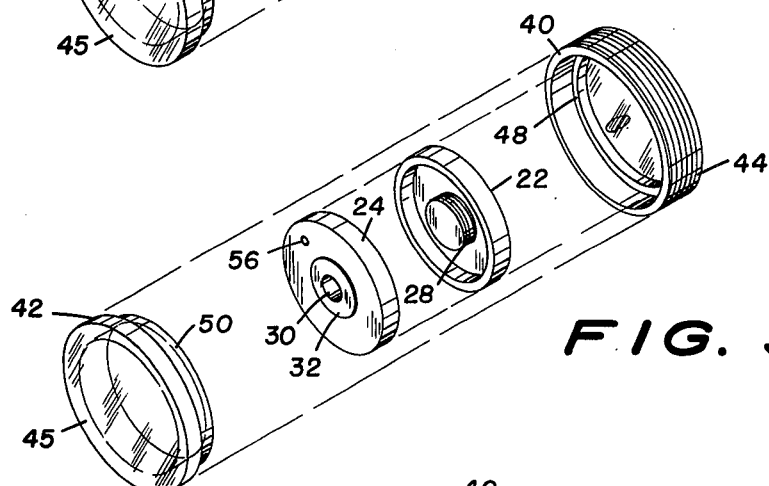
Figure 3C:
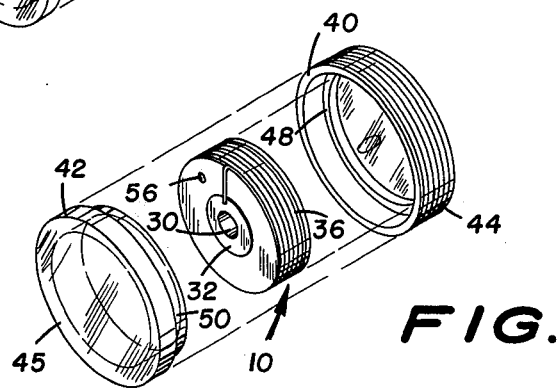
Figure 3D:
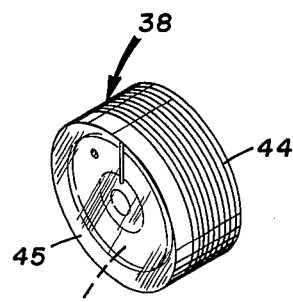

Referring now to FIGS. 1 and 2, the present implantable transducer is seen at 10 to be positioned within a burr hole 12 in the skull 14 of an individual who has need for monitoring of the intracranial pressure. The lower face of the transducer 10 is seen to be positioned against the dura 16, a membrane which lies beneath the skull 14 and above the subarachnoid space, i.e., the space between the skull 14 and the brain. The transducer 10 can be mounted as will be described in detail hereinafter to bear against the dura 16 without deflecting the dura downwardly enough so as to obliterate the subarachnoid space below the transducer. The dura 16 may therefore act to transmit subdural cerebral spinal fluid pressure to the transducer 10. Pressure sensed by the transducer 10 is measured by an external detector 18 which is positioned externally of the scalp over the implanted transducer 10, the detector 18 being electrically connected to a recording and alarm monitor 20. Through use of the monitor 20 in a manner to be described hereinafter, a continuous record of intracranial pressure can be made. Additionally, a visual or audio alarm can be integrated into the monitor 20 to provide a signal when intracranial pressures reach dangerously high (or low) levels.

The structure of the transducer 10 can best be seen in FIGS. 3a through 3d and 4 to comprise two disc-like sections 22 and 24 which are bonded together to form a hollow circular cylinder. Each section has a central aperture 26 formed in its planar face, the apertures 26 respectively receiving bellows 28 and 30 thereinto. The sections 22 and 24 are formed of a ceramic or other non-porous material and are suitably bonded together, such as with glass frit or with epoxy cement. The bellows 28 and 30 are preferably formed of gold-plated nickel. The bellows 28 and 30 are each formed with an annular flange 32 surrounding the open end thereof, the flange 32 being bonded, such as by epoxy, to the peripheral portion of the planar face of each section 22 or 24 which surrounds each of the apertures 26. The planar closed end of each of the bellows 28 and 30 is disposed toward the interior of the enclosed chamber 34 formed on bonding together of the sections 22 and 24, the said closed ends extending into the chamber from opposite sides thereof and being spaced apart by a finite, pre-determined spacing as will be described in greater detail hereinafter.

The hollow circular cylindrical chamber 34 defined by the sections 22 and 24, when fully closed by bonding of the bellows 28 and 30 into respective apertures 26, forms a reference pressure enclosure in which is entrapped a given mass of a gas (or other compressible non-toxic fluid), the pressure of which mass of gas is used as a reference pressure relative to the pressure of the transducer's environment, i.e., within the skull 14 in which the transducer 10 is disposed. The gas preferably takes the form of pure nitrogen having condensable gases such as water vapor removed therefrom. The gas within the chamber 34 is sealed therein at standard atmospheric pressure. Leakage of gas from the chamber 34 or seepage of other fluids into the chamber 34 is to be prevented. Bonding of the flanges 32 of the bellows 28 and 30 to the sections 22 and 24 must therefore be accomplished so as to minimize changes in this reference pressure gas volume. A metallization ring can be formed around each of the apertures 36 and flange 26 soldered thereto. Alternatively, the flanges 26 can be bonded to the ceramic material with epoxy. Although epoxy is a more porous material than solder, the epoxy joints have a high ratio of path length to diffusion cross-section compared to that of the ceramic portion of the transducer 10. Simple epoxy bonding is therefore considered to be adequate and economically attractive since base-line drift, i.e., change in the reference pressure, is sufficiently slight with such bonding as to be tolerable.

The assembled sections 22 and 24 further have an inductance coil 36 wound thereabout, the ends of the coil 36 being respectively soldered to the bellows 28 and 30 to form a passive resonant circuit in which the closed ends of the bellows lie in proximity to each other to form the capacitive portion of the circuit. The inductance coil 36 preferably is formed with eight turns. The coil 36 can be formed of silver, platinum, copper, or other highly conductive material. The conductive material should have low electrical resistance in order to provide a high Q to the resonant circuit of which the coil 36 forms a part. Silver and platinum would be preferred due to the less toxic properties of these conductors relative to copper. Platinum is least toxic of the three conductors mentioned, although the relatively higher resistance of the platinum causes some loss of Q. An increase in pressure externally of the transducer 10 acts to elongate both of the bellows 28 and 30, thereby bringing the closed ends thereof closer together to increase the capacitance and to lower the resonant frequency of the circuit. Pressure changes can thus be monitored externally of the transducer 10 by measurement of the frequency at which the circuit absorbs energy from an externally imposed electromagnetic field.

As discussed briefly hereinabove, the transducer 10 must exhibit sufficient elastic compliance such that a measurable deformation will result from relatively small changes in intracranial pressure. At the same time, the enclosure for the entrapped gas must be extremely non-porous so that the mass of gas entrapped will not change appreciably during the useful life of the transducer 10. Further, the transducer 10 must be electrically non-conductive so that the resonant circuit formed by the bellows (28 and 30) and the inductance coil 36 will be shielded from the externally imposed electromagnetic field. The use of plastic material for the sections 22 and 24 would be sufficiently compliant and non-conductive but prove to be too porous. The use of non-porous and non-conductive glass proves to be unsatisfactory due to the non-compliant nature of the material in structurally adequate wall thicknesses. The requirement for low porosity, low electrical conductivity, and relatively high elastic compliance are met in the transducer 10 by forming the major portions of the planar faces the enclosure (formed by the sections 22 and 24 with central apertures 26) of non-porous and non-conductive ceramic material and by forming reduced portions of the planar faces with metal, i.e., the bellows 28 and 30, the metal being non-porous and compliant. Since the metal is also electrically conductive, a portion of the magnetic field absorption cross-section of the transducer 10 is shielded. However, by controlling the percentage of the surface area of the planar faces of the transducer 10 which is subtended by the metal bellows 28 and 30, the percentage of the magnetic field absorption cross-section which is shielded to the externally imposed electromagnetic field is readily held within acceptable limits. The area of the metal portion forming the planar faces of the transducer 10 is preferably held to approximately 20% in order to retain sufficient elastic compliance while limiting shielding as aforesaid. This shielding diminishes the coefficient of coupling between the transducer 10 and external monitoring apparatus to be described, thereby reducing slightly the implantation depth at which the resonant frequency of the transducer 10 can be measured.

The transducer 10 is enclosed within a casing 38 formed of two cylindrical half-sections 40 and 42, the half-sections 40 and 42 being boned together to form the closed cylindrical casing 38. The casing 38 is preferably formed of a suitable bio-compatible plastic such as Lexan, a product of General Electric Inc., or Polysulfone. The half section 40 is seen to be formed with threading 44 over the cylindrical surface thereof and with slots 46 in the upper planar face 43 thereof, the slots 46 not extending through the face. The half-section 40 is bonded to the half-section 42 using a suitable solvent and plastic grit of the type of plastic employed as the material of which the half-sections are formed. The lower planar face 45 of the half-section 42 is typically made less thick than the upper planar face 43, the face 45 being as thin as is structurally practical in order to aid in pressure transfer across said lower face. For example, if the half-sections 40 and 42 are formed of polysulfone, a grit of polysulfone dissolved in dichloroethane is used to cement the half-sections 40 and 42 together. Mating inner and outer annular shoulders 48 and 50 form a lap-joint 52 which seals the casing 38 more securely.

The spacing internally of the casing 38 and externally of the transducer 10 is filled with a suitable fluid 54, such as medical grade silicon liquid, which transmits external pressure on the casing 38 to the bellows 28 and 30. The fluid 54, in addition to its ability to transmit pressure, should be chosen to have a low dielectric constant in order to minimize stray capacitance, to have a low ability to absorb moisture, and to be non-toxic. The casing 38 acts at its most basic level to isolate the circuit formed by the bellows and the coil 36 from conductive body fluids which would short-circuit the bellows capacitance.

Since a number of the transducers 10 would be manufactured in order to meet the clinical needs mentioned hereinabove. it is believed necessary to discuss calibration and manufacturing control considerations which are useful to a reasonable practice of the invention. Calibration of the transducer 10 is essentially a matter of control of the spacing of the closed ends of the bellows 28 and 30. At atmospheric pressure and at usual body temperature, the closed ends of the bellows are to be spaced 0.004 inch apart. Control of the spacing between the closed ends of the bellows is principally a matter of controlling the thickness of the epoxy bond between the two ceramic sections 22 and 24. It is deemed preferable to epxoy bond the sections 22 and 24 together rather than to fire a joint therebetween using glass frit, since epoxy bonding can be done after the bellows 28 and 30 are mounted on the sections 22 and 24 whereas firing of the glass frit requires that the heat-treatable bellows be mounted after the bonding between the sections is accomplished. The spacing uncertainty introduced by the bonding of the bellows 28 and 30 to the ceramic sections 22 and 24 can be determined electrically and eliminated by honing the ceramic sections on a diamond dust-impregnated copper flat. Honing is performed on the surfaces of the sections 22 and 24 which are later bonded together.

Control of the reference pressure within the sealed transducer 10 requires the epoxy bonds between the ceramic sections 22 and 24 to be formed and cured, such as by baking, before final closure of the chamber 34. A small vent hole 56 formed in one of the sections, such as in the section 22, is used to seal the chamber 34 in a manner to be described more fully hereinafter. Compensation for error in spacing between the closed ends of the bellows 28 and 30 requires a bias in the closure temperature at the rate of 10.8° C per milli-inch of spacing error. The integrity of the bonded joints must also be insured since even a minute rate of leakage into or from the chamber 34 results in an unacceptable rate of drift of the reference pressure. Thus, the chamber 34 is leak tested after closure of the vent hole 56 and allowance for the entrapped gas to reach room temperature. As the entrapped gas in the sealed chamber 34 cools to room temperature, the resonant frequency of the circuit diminishes approximately 8.4 MHz. If any gross leaks are present, the frequency will drift back to the body temperature value. If the room temperature frequency remains stable, indicating no gross leaks, the transducer 10 is then fine leak tested by soaking the transducer in pressurized helium for a period of time to allow helium to enter through any microscopic leak which might exist. The transducer 10 is then placed in a helium leak tester vacuum chamber to detect escape of helium for the chamber 34. If no helium is detected, the transducer 10 is considered to be leak free.

The operation of the transducer 10 can be described by the following mathematical relationships, the pressure $P_o$ external of the transducer being related to the pressure $P_i$ by the following:

$$P_o = P_i + \frac{k}{A}(X_o - X)$$

where:
$k$ = the spring constant of the bellows 28 and 30;
$A$ = cross-sectional area of the bellows closed end;
$X_o$ = neutral (unstressed) position of the bellows (half the separation of the bellows); and,
$x$ = the stressed position of the bellows.

Since the volume change caused by bellows deformation is negligible, the internal pressure $P_i$ can be expressed in terms of temperature as follows:

$$P_i = \frac{P_c}{T_c} T$$

where $P_c$ and $T_c$ are respectively the closure pressure and temperature at the time the vent hole 56 in the transducer 10 is sealed. The ideal value for these last two parameters are 10,336 mm H$_2$O (760 mm Hg) and 558°R (body temperature, absolute). Hence the temperature sensitivity of the transducer 10 is 18.5 mm H$_2$O/F°. and the formula giving the pressure correction ($P_T$) for body temperature ($T_B$) is:

$$P_T = 18.5 (T_B - 98.6)$$

The distance (X in milli-inches) of the surface of the bellows 28 and 30 from the midpoint between the bellows can be given in terms of the resonant R-F frequency ($\omega$):

$$X = \frac{\frac{1}{2} \omega^2 LK}{1 - \omega^2 LC_s}$$

$L$ = inductance (1.4 × 10$^{-6}$ henries);
$K$ = a constant (4.039); and,
$C_s$ = stay capacitance ($\mu\mu$F).

The general equation can now be written:

$$P_{BP} + P_A = \frac{P_c}{T_c} T = \gamma \frac{f_o^2 - f^2}{(1 - \beta f_o^2)(1 - \beta f^2)}$$

where:
$P_{BP}$ = barometric pressure (mm H$_2$O);
$P_A$ = applied pressure (mm H$_2$O);
T = temperature (F. degrees absolute)

$$= 2\pi)^2 \frac{k}{A} \frac{k}{2} L$$

$= 2\pi)^2 LC_S$ ; and
$f_o$ = frequency under standard conditions of pressure (10,366 mm H$_2$O) and temperature.

The last three numbers $\gamma$, $\beta$, and $f_o$ are sufficient to describe completely the performance of the transducer 10. The value for $f_o$ is measured directly and the values for $\gamma$ on $\beta$ are determined from two frequency readings $f_1$ and $f_2$ at two different pressure readings $P_1$ and $P_2$ made at a known temperature and barometric pressure. The frequency response of the transducer 10 versus the pressure acting on the transducer 10 is shown graphically in FIG. 7.

Figure 5:
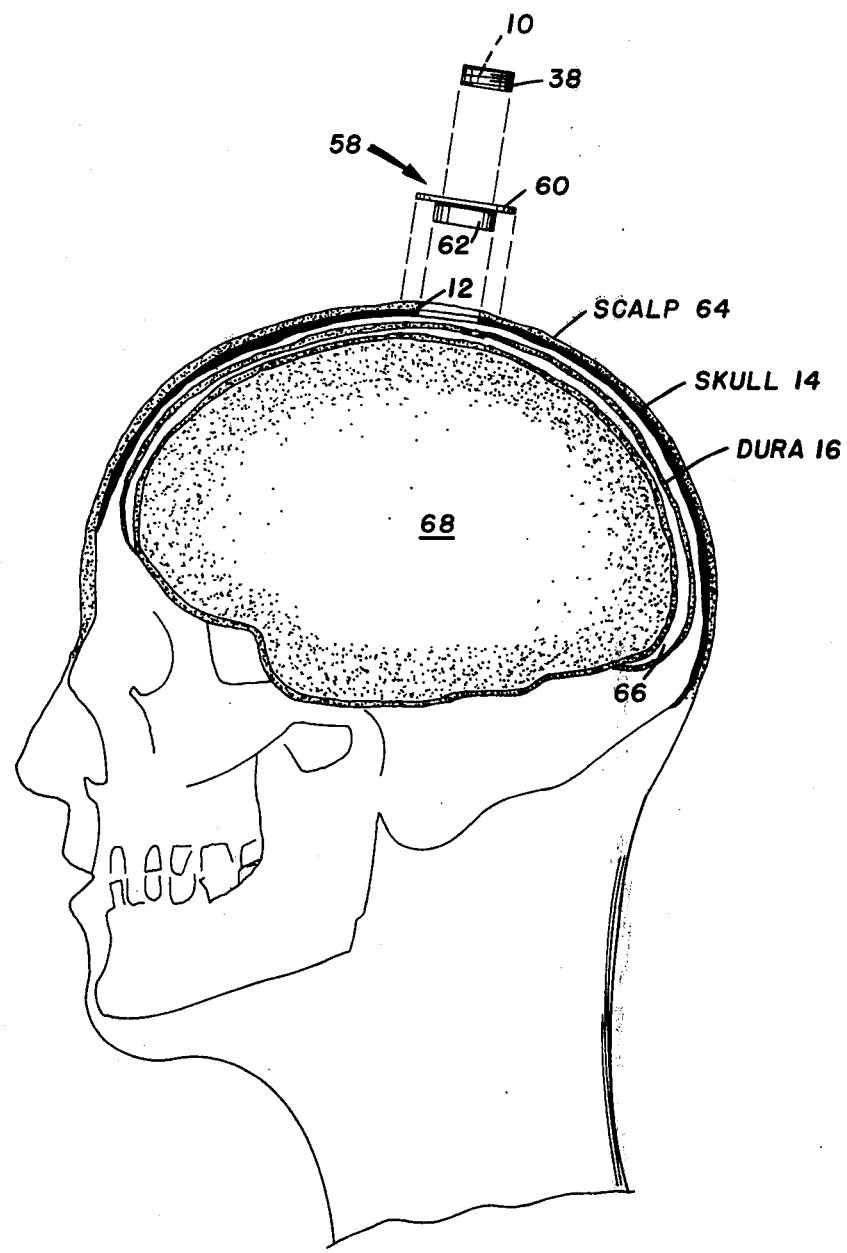
FIG. 5 is a schematic illustrating in part the manner in which the transducer is mounted in the cranium.
Figure 6:
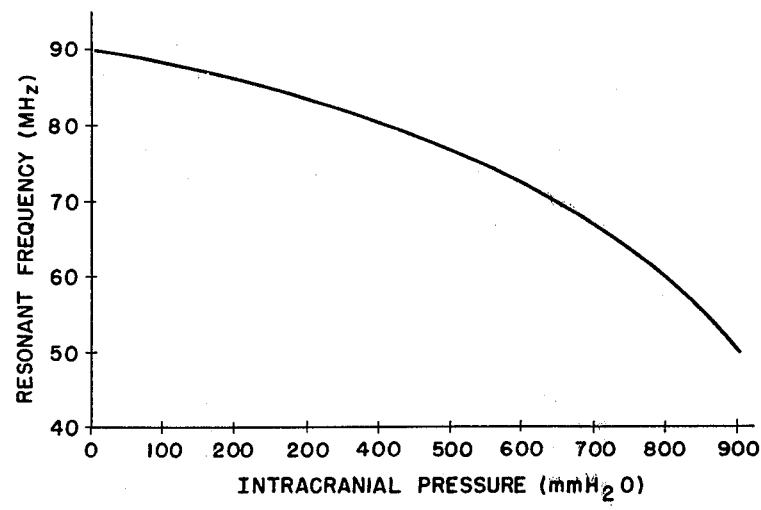
FIG. 6 is a graph illustrating the resonant frequency response of a typical transducer versus the sensed intracranial pressure.

Referring now to FIGS. 1, 2, and 5, the transducer 10 encased in the casing 38, which will be referred to hereinafter as the "encased transducer 10", is seen to be held within a cranial burr hole 12 by means of a collar 58. Implantation of the transducer 10 can be made under local anesthesia through a curvilinear incision in the scalp 64. The burr hole 12 is made in the skull 14, usually as the result of treatment for a siutation which incidentally requires monitoring of intracranial pressure, according to known procedures: Typically, an air-driven trephine or brace trephine is used to make the hole 12, the cavity in the skull 14 being trimmed with a curette to expose a circular area of dura. Bone wax is used to stem bleeding from the walls of the burr hole 12 and a bipolar coagulator is used to stop any bleeding which may exist on the surface of the exposed dura 16. The collar 58 is then attached to the skull 14, an annular flange 60 on the upper end of the collar resting on the table of the skull 14. The flange 60 has peripherally spaced apertures (not shown) therein which allows suturing of the collar 58 to the periosteum or bone. In the event the periosteum is not available, the galea tissue is turned over the flange 60 as a flap and secured with interrupted sutures. The scalp margins are approximated for subsequent wound closure. An annular cylindrical neck 62 which forms the remaining portion of the collar 58 extends into the burr hole 12 and is threaded internally at 63 to receive the threads 44 on the outer cylindrical surface of the casing 38 of the encased transducer 10. The encased transducer 10 can thereby be screwed into the neck 62 of the collar 58 to a depth sufficient to cause the lower planar face 45 of the casing 38 to bear against the dura 16 as seen clearly in FIG. 2. The encased transducer 10 is rotated within the collar 58 by means of a two-pronged wrench, shown in FIGS. 8 and 9 to be described hereinafter, which mates with the slots 46 in the upper planar face 43 of the half-section 40. The scalp 64 is then closed over the implantation thus formed. It should be understood that the encased transducer 10 can be implanted in a number of other ways. For example, the encased transducer 10 can be simply placed in the burr hole 12 and pushed to one side thereof between the dura 16 and the skull, the burr hole 12 then being sealed with a plug or with bone wax. Alternatively, the encased transducer 10 can be implanted subdurally. According to the preferred manner of implanting the encased transducer 10 as described above and as will be further described hereinafter, the dura 16 is not deflected downwardly by the lower planar face 45 of the casing 38 sufficiently to obliterate the subarachnoid space 66 below the casing 38 between the dura 16 and the brain 68. The dura 16 can then act as a second diaphragm to transmit the subdural cerebral spinal fluid pressure to the encased transducer 10.

As has previously been briefly described, the external detector 18 is brought into spaced relationship to the implanted transducer 10 on closure of the scalp 64. The detector 18 is usually taped on the surgical dressing which overlies the site of the implanted transducer 10. As will be soon described in detail, the detector 18 interrogates the implanted transducer 10 by directing electromagnetic energy into the transducer, the frequency at which the transducer absorbs the incident electromagnetic energy being a measure of the intracranial pressure sensed by the transducer. The detector 18 is connected to the monitor 20 as aforesaid, the monitor 20 operating continuously to provide a permanent record of the intracranial pressure. The monitor 20 can take the form of medical monitoring apparatus now commercially available. Desired functions which are within the art can be readily incorporated into the monitor. For example, visual or auditory alarms can be caused to operate if the sensed pressures reaches certain predetermined levels. The monitor 20 can be designed, however, so that it will not respond to momentary increases in pressure such as are typically brought about by coughing or straining. Since the transducer 10 essentially acts as a small barometer and is thereby responsive to absolute pressure, correction for barometric pressure can be included in the monitor 20 itself. Alternatively, corrections can manually be made in response to barometric pressure changes.

Prior to implantation, the encased transducer 10 (as well as the collar 58) is to be sterilized internally as well as externally. The transducer 10 cannot be autoclaved because the great heat would rupture the bellows 28 and 30. While the encased transducer 10 can be brought to a temperature of 120° C and held at that temperature for an extended period of time, sterilization by radiation appears to be the best procedure.

Figure 7:
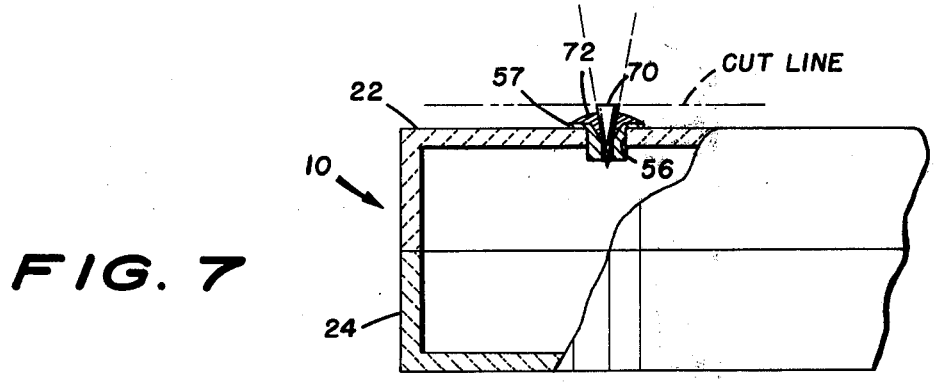
FIG. 7 is an elevation in partial section of a portion of a transducer illustrating the sealing thereof.

Referring now to FIG. 7, a preferred method for sealing the transducer 10 is shown. As aforesaid, a vent hole 56 is formed in one of the ceramic sections 22 or 24. After assembly of the bellows 28 and 30 to the sections and bonding together of the sections, the specific mass of gas is finally entrapped within the chamber 34 by sealing of the vent hole 56. The vent hole 56 is best sealed by providing a thin annular metal insert 57 within the hole 56. The insert 57 has sloping inner cavity walls and may preferably be formed of brass. The insert 57 can be simply coated with soft solder while leaving the hole 56 open. The transducer 10 would then be brought to body temperature and the solder coating touched with a hot iron to close the hole 56. However, it is believed preferable to first insert a pin 70 into the hole 56 as shown in FIG. 7. Solder 72 is then applied to the sides of the pin 70, the solder 72 adhering also to the metal insert 57 to seal the hole. The pin 70 has sloping surface walls which mate with the sloping walls of the cavity in the insert. The transducer 10 is brought to a desired temperature, i.e., body temperature modified by 0.42° C per millimeter of mercury atmospheric pressure deviation from standard. The use of the pin 70 prevents gaseous elements from the solder from diffusing into the chamber 34, thereby altering the reference pressure provided by the gas entrapped therein. The pin 70 can be severed just above the solder joint after sealing.

Figure 10:
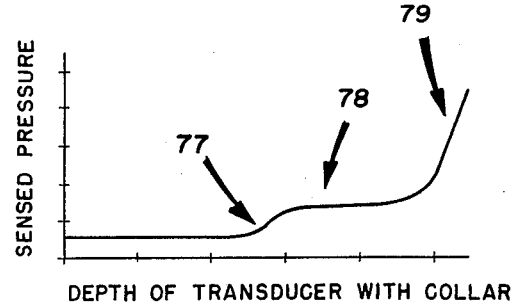
FIG. 10 is a graph illustrating the pressure response of the transducer at varying implantation depths in the cranium.
Figure 8:
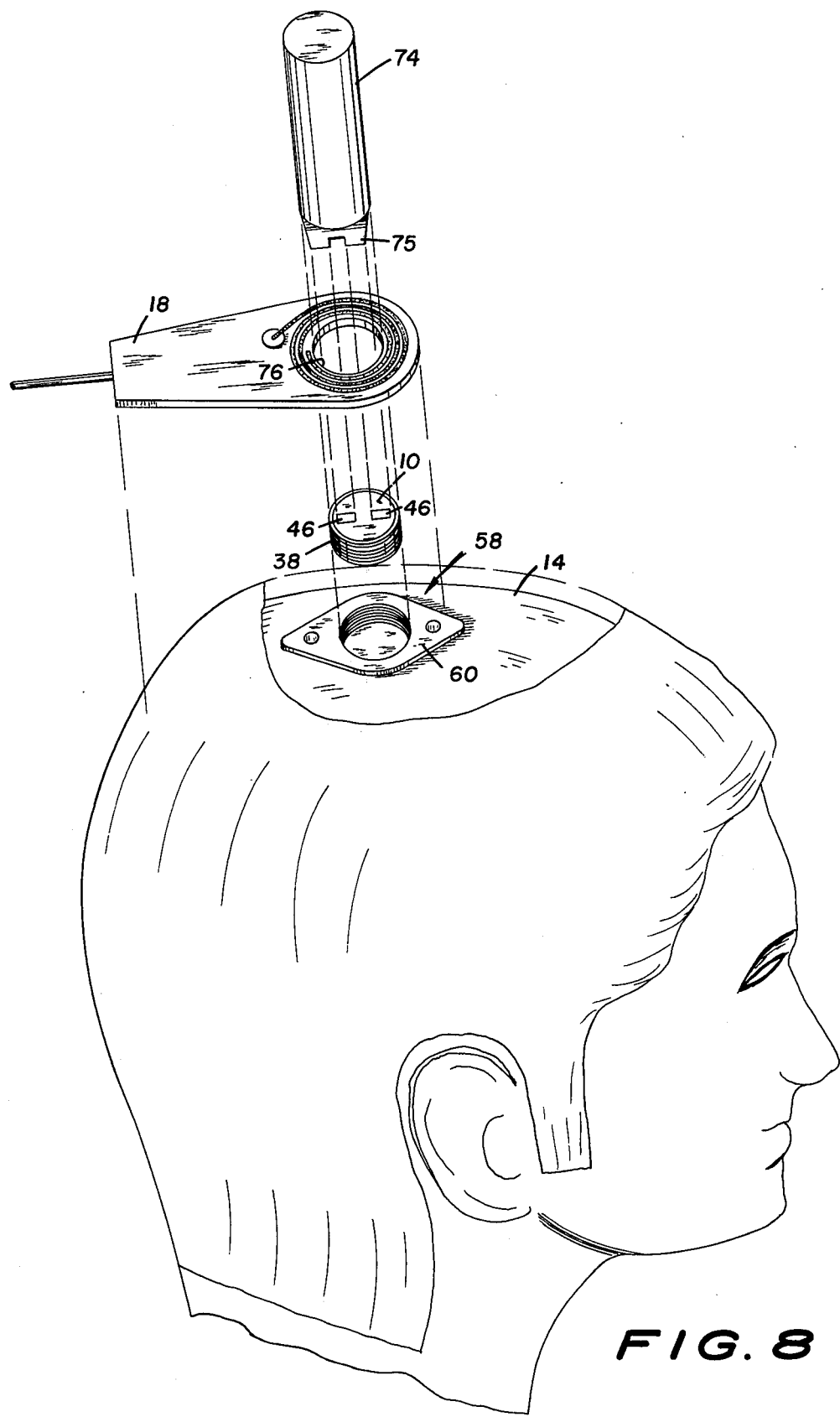
FIG. 8 is an idealized assembly perspective illustrating the arrangement of elements used to implant the transducer.
Figure 9:
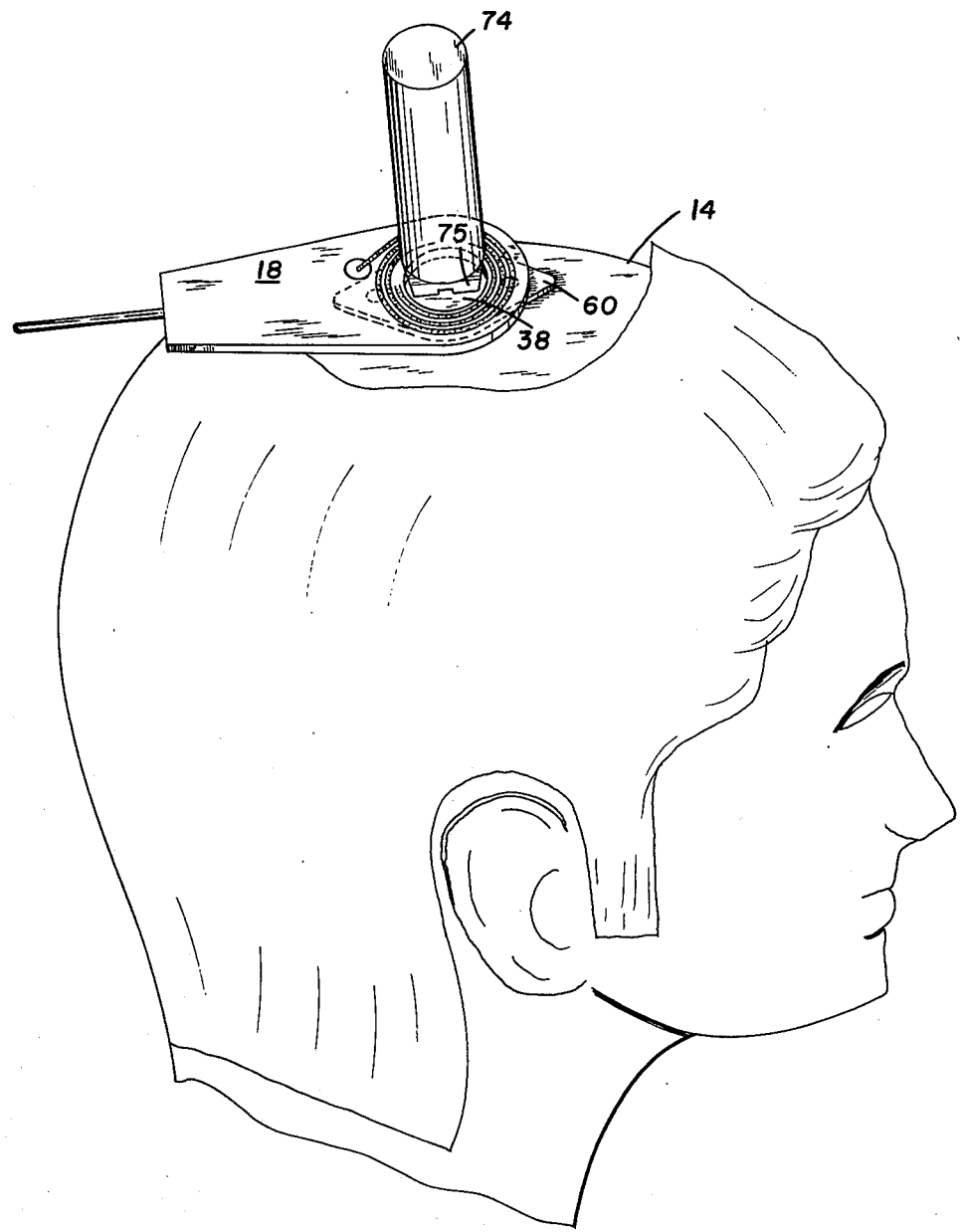
FIG. 9 is an idealized perspective illustrating the method employed to position the transducer properly in the cranium.

The method of implantation of the transducer 10, as described relative to FIGS. 1, 2, and 5, can be seen in further detail through the illustration provided by FIGS. 8 and 9. In FIG. 8, a subject is shown with the collar 58 sutured to the skull 14, the transducer 10 initially having been manually threaded into the collar 58. As seen in FIGS. 8 and 9, a tool 74 having spaced pins 75 which mate with the slots 46 in the casing 38 is used to rotate the encased transducer 10 further into the threaded collar 58 toward contact with the dura 16 as aforesaid. In order to determine when full contact occurs between the lower planar face 45 of the casing 38 and the dura 16, the detector 18 is provided with a central aperture 76, inductance coils which are a part of the circuitry of the detector 18 and which will be described hereinafter lying about the periphery of the central aperture 76. The detector 18 is placed over the encased transducer 10 and the collar 58, the aperture 76 being sufficiently large to allow the tool 74 to be fitted into contact with the encased transducer through the aperture 76. The tool 74 is rotated to cause the encased transducer 10 to be seated more deeply within the threaded collar 58. While the tool 74 is thus being operated, the detector 18 is used to monitor the pressure sensed by the encased transducer 10. Referring now to FIG. 10, the pressure sensed by the transducer 10 is shown versus the depth of the transducer within the collar 58. The pressure sensed by the encased transducer 10 remains relatively constant until the lower planar face 45 of the casing 38 initially contacts the dura 16, at which time the sensed pressure increases abruptly as seen at 77. As the encased transducer 10 is further moved toward the dura 16, the sensed pressure first continues to increase and then levels off to form a plateau at 78 in the pressure-depth curve of FIG. 10. This plateau indicates that full contact between the lower planar face 45 of the casing 38 and the dura 16 has been achieved. Substantial movement of the encased transducer 10 in an inward direction eventually causes a second abrupt increase in pressure, as seen at 79, this pressure increase indicating that the subarachnoid space between the dura 16 and the brain has been obliterated, the encased transducer 10 therefore having been inserted too deeply into the cranial cavity. The tool 74 could therefore be used to withdraw the transducer 10 outwardly within the collar 58 to the desired depth as shown by the re-establishment of the plateau 78 on the depth-pressue curve of FIG. 10. In practice, once the plateau 78 is established during simultaneous insertion of the encased transducer 10 and monitoring thereof through use of the detector 18, the transducer 10 is considered to be located properly and the tool 74 and the detector 18 are removed. The wound is then closed as described hereinabove and intracranial pressure is monitored externally through use of the detector 18 and the monitor 20.

As indicated above, the transducer 10 contains a passive resonant circuit formed by the bellows 28 and 30, which act as a capacitor, and the coil 36, which acts as an inductor, the circuit having a high Q. The natural frequency of the circuit is influenced by the pressure "seen" by the encased transducer 10, the pressure of the gas trapped within the chamber 34 being compared to this environmental pressure. An increase in this environmental pressure, i.e., the intracranial pressure, causes the bellows 28 and 30 to elongate to bring the closed ends of said bellows closer together, thereby increasing the capacitance of the resonant circuit and, accordingly, lowering the r-f resonant frequency of the circuit. Measurement of any change in the r-f resonant frequency of the resonant circuit is made through the scalp 64 (and medical dressings) by use of the detector 18 and monitor 20. The detector 18 is placed over that location on the scalp which surmounts the implanted transducer 10. The resonant frequency of the transducer circuit is then determined by subjecting the circuit to a frequency swept RF signal from the detector 18, the frequency at which the electromagnetic energy is most efficiently coupled into the transducer circuit, wherein said energy is dissipated by resistive losses, then being detected by the detector 18.

A well-known device such as a grid-dip oscillator (not shown) can be employed to interrogate the implanted transducer 10, the oscillator being used with associated means for varying frequency over a range which includes the resonant frequency of the transducer circuit and additional means for identifying the frequency at which a grid current dip occurs. Such means are known in the art. A grid-dip oscillator essentially is itself a resonant circuit, i.e., a circuit with high Q, which consists of a capacitor and an inductance coil in an oscillator circuit. However, this well-known device has poor output regulation, the oscillation amplitude being markedly diminished by even slight loading. Further, such a device must be continuously tuned manually and does not display dynamic pressure changes.

Figure 11:
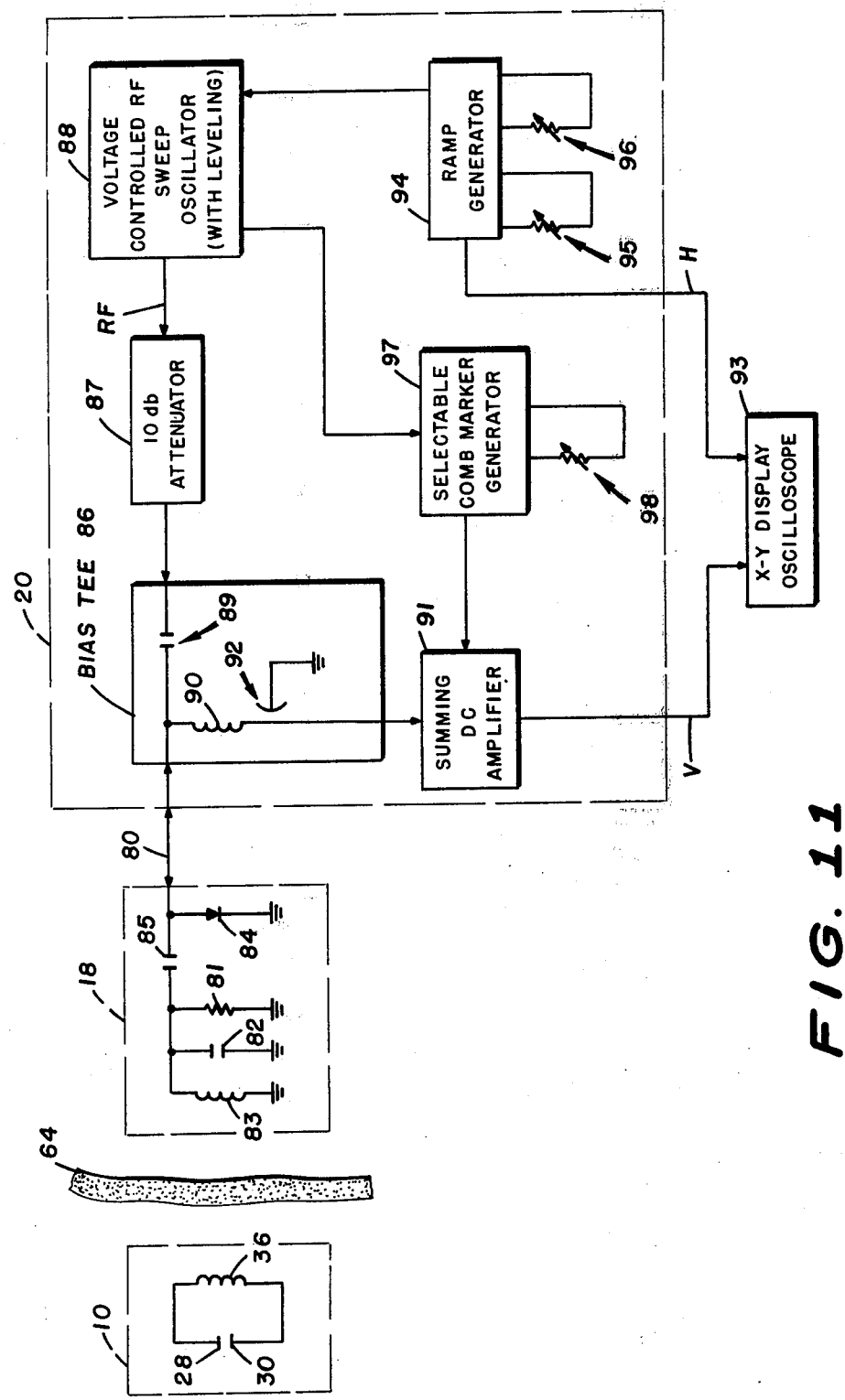
FIG. 11 is a block diagram illustrating the electrical components of the transducer, the external detector, and the external monitoring apparatus used to detect and monitor the resonant frequency of the transducer.

The transfer of energy by inductive coupling from an inductor external of the cranium, i.e., in the detector 18, to the inductance coil 36 in the transducer 10 can be more efficiently and effectively accomplished through use of the system shown in FIG. 11. The detector 18 is seen to be electrically joined to the monitor 20 by means of a single coaxial transmission line 80 which conveys RF signals from the monitor 20 to the detector 18 and simultaneously returns the signal detected by detector 18, which detected signal appears as a DC voltage, to the monitor 20. Although separate coaxial cables could be used to separately convey the RF input and the DC output, the presence of two separate cables attached to the detector 18 results in reduced flexibility of the combination, the detector 18 thereby being less handy to use for routine monitoring.

The RF input to the detector 18 typically has a characteristic impedance of 50 ohms, the signal being driven by a swept frequency signal source in the monitor 20 which has an output impedance of 50 ohms. A 50 ohms resistor 81 is present in the circuit of the detector 18, the resistor 81 minimizing the SWR over the operating frequency band so that reflections do not cause extraneous frequency dependent peaks and nulls. A parallel resonant LC circuit comprised of capacitor 82 and inductor 83 is placed across the transmission line 80. The bandwidth of this resonant circuit is intentionally made large by using a large L to C ratio along with the heavy resistive loading caused by the resistor 81 in parallel with the 50 ohm RF source resistance, inductor losses being comparatively negligible. The inductor 83 is physically constructed and positioned in the detector 18, to maximize inductive coupling with the inductance coil 36 in the implanted transducer 10. The inductor 83 essentially takes the form of a flat ribbon spiral as seen on the surface of the detector in FIGS. 8 and 9. A diode 84 detects the RF signal appearing across the inductor 83 and produces a DC voltage output which is proportional to the existing RF voltage. The diode 84 is positioned in the detector circuit so that this resulting DC voltage appears on the RF input transmission line. A low RF impedance coupling capacitor 85 passes the RF signal to the resistive termination and to the broadband resonant LC netowrk. The capacitor 85 also blocks the DC voltage signal from being short circuited to ground through the inductor 83.

In normal operation the RF signal source in the monitor 20 (to be described in detail hereinafter) is swept linearly from 50 MHz to 100 MHz at a 60 Hz rate and provides a constant output power level of about 1 milliwatt (OdBm). The output power level is preferably maintained at a constant level over the sweep range to within ±0.25 dB. In the absence of inductive coupling, the RF voltage at the detector 18 remains constant throughout the sweep range. The resulting DC output voltage is likewise constant.

When the resonant circuit of the implanted transducer 10 is coupled to the LC circuit of the detector 18, energy is coupled from the detector 18 to the transducer 10 only at the resonant frequency of the transducer. When this energy transfer occurs, an accompanying reduction in the RF voltage appears across the inductor 83. This reduction can be envisioned as either a power transfer which loads down the source of the RF voltage or, equivalently, as an impedance transformer which reflects a low value resistnce across the inductor 83. The magnitude of the RF voltage drop is dependent primarily on the amount of inductive coupling which is maximized when the two inductors, i.e., the coil 36 and the inductor 83, are positioned coaxially in the closest possible proximity. The loading effect occurs only at the resonant frequency of the transducer 10, consequently, as the applied RF signal is swept across the operating band, the circuit of the detector 18 will respond to a dip in RF voltage across the inductor 83 as the swept signal passes through the resonance of the transducer 10. The bandwidth of this dip is determined jointly by the Q of the resonant circuit of the transducer 10 and by the amount of inductive coupling. Low Q and tight coupling increase bandwidth and impair resolution of the resonant frequency. By correlating the occurrence of the voltage dip with the RF frequency of the source of sweep generation, the frequency of resonance is determined, the intracranial pressure being related thereto.

In order to recover the DC voltage signal from the transmission line 80 and to prevent said signal from being loaded by the RF signal source, a bias tee 86 is provided in the transmission line 80, the bias tee 86 being integrated into the monitor 20. The bias tee 86 receives the RF voltage signal through a 10 db attenuator 87 from a voltage controlled RF sweep oscillator 88. The bias tee 86 essentially consists of a low RF impedance coupling capacitor 89 which passes the RF voltage signal from the sweep generator 88 and blocks the DC voltage signal returning from the detector 18. The DC voltage signal is shunted through a radio frequency choke 90 in the bias tee 86, the choke 90 appearing as a negligible high impedance to the RF signals while passing the DC signal to a DC amplifier 91. A low RF impedance feed through capacitor 92 positioned between the choke 90 and the amplifier 91 acts to prevent RF signals from being passed on to the amplifier 91. The amplifier 91 can typically provide a 10,000 ohm DC load to the detector 18 and thereby produces an inverting DC gain of 20. The DC output of the detector 18 is typically on the order of −50 mV, thereby producing a +1.0 volt output from the amplifier 91. Typical components values in the bias tee 86 are 2,000 pf for the capacitor 89, 2.2μ h for the RF choke 90, and 1,000 pf for the capacitor 92. In the detector 18, typical component values are 1,000 pf for the capacitor 85, 51 ohms for the resistor 81 and 10 pf for the capacitor 82. The diode 84 ca be a Schottky barrier type, a suitable inexpensive commercial version of which is the HP 5082–2800.

The inductor 83 takes the form of a spiral inductance coil as seen in FIGS. 8 and 9, which coil can be formed on a flat PC-type board. In such a typical construction, the inductor 83 would exhibit an inductance of 0.305 microhenrys and would have a self resonant frequency of about 270 MHz, thereby indicating a stray capacitance of about 1.1 picofarad. When using an additional 10 pf capacitor, the circuit of the detector 18 resonates at about 87 MHz, such resonance providing a nearly symmetrical, slightly rounded response from 50 MHz to 100 MHz with only a slight midband peak.

The monitor 20 is configured to drive a commercial X-Y disply oscilloscope 93, such as the Telonic Model 121 or the Wavetek Model 1901A. The monitor 20 itself can consist primarily of a commercially available RF sweep generator such as the Wavetek Model 1050A sweep generator, this commercial unit being modified in several ways. Primarily, this commercial sweep generator is modified by adding the bias tee 86 for extraction of the DC voltage signal from the detector 18 and by adding the DC amplifier 91 for increasing the DC signal. Frequency marker signals to be described hereinafter are also added to assist in signal processing. Other functions added to this commercial sweep generator include: (1) restriction of the frequency range of the center frequency control to a desired band; (2) replacement of the RF output step attenuator with the 10 db attenuator 87 to set the output level at 0 dBm; (3) replacement of the RF output vernier control with a fixed setting; (4) removal of the demodulator input connection; (5) re-positioning, calibration, and limiting the range of the sweep width control; (6) replacement of the marker width control with a fixed value, (7) rewiring of the AC power switch to break both sides of the line; and, (8) fabrication of a control panel with controls labeled and positioned to facilitate use of the monitor 20.

The monitor 20 is then configured as specifically seen in FIG. 11, the sweep oscillator 88 providing an RF output restricted to the frequency range of approximately 50 MHz to 100 MHz. An output level of about + 10 dBm is controlled and maintained at a constant level across the sweep range of the oscillator 88 by an internal active leveling circuit (not shown). A frequency control voltage which is fed into the oscillator 88 is obtained from ramp generator 94, the ramp from the generator 94 being shaped to compensate for non-linearities in the oscillator 88 so that a linear frequency sweep results. Sweep rate is fixed at the AC line frequency (60 Hz). Center frequency of the RF sweep is operator adjustable by a center frequency variable resistor 95 over a range from 50 MHz to 100 MHz. The operator would typically set the center frequency to nearly coincide with the resonant frequency dip displayed on the display oscilloscope 93. The sweep width (or frequency span) is also operator adjustable by a sweep width variable resistor 96 to a nominal range of b 1 MHz to 50 MHz. The operator can adjust the sweep width to obtain the desired horizontal display "magnification" to facilitate resolution of the resonant dip frequency. The resulting sweep voltage is ramped symmetrically both up and down. During the down or retrace sweep, the output amplifiers (not shown) of the oscillator 88 are electronically switched off in order to remove the RF output. A zero output reference is thus produced during this retrace interval and appears as a straight baseline on oscilloscope 93. The ramp generator 94 also provides a linear ramp (triangular) voltage which is fed to the oscilloscope 93 to be used as the horizontal drive signal.

The leveled RF output from the sweep oscillator 88 is attenuated by the attenuator 87 to about 0 dBm. At this drive level, the transfer characteristic of the detector 18, i.e., DC out vs. RF power in, begins to become less exponetial, i.e., more linear. Increasing the drive level would also increase the amplitude of the resonance dip of the detector 18. However, the average DC output would correspondingly increase in a significantly greater fashion, thereby resulting in the magnitude of the dip being proportionately smaller in relation to the DC level away from resonance. The summing DC amplifier 91 combines the DC output from the bias tee 86 with frequency marker output signals generated by a selectable comb marker generator 97. Demodulated siganls from the detector 18 are inverted and amplified by 20 while the marker signals are inverted and amplified by a factor of unity. The resulting signal is fed from the amplifier 91 to the oscilloscope 93 as the vertical input thereto. The marker generator 97 consists of three separate comb frequency generators (not shown), any one or combination of which can be selected by an operator through use of a marker size variable resistor 98. The comb frequency generators are used to determine the frequency at which the resonant dip appears on the display oscilloscope 93. The comb generators produce crystal controlled marker signals having 1 MHz, 10 MHz, or 50 MHz spacing. These marker signals are compared with a sample of the swept RF signal through connection to the oscillator 88. When an audio beat frequency is produced by the two signals, the marker generator 97 produces a clipped output marker signal.

In order to protect the patient from electrical shock hazards, the monitor is isolated from AC power lines by the use of isolation transformers (not shown) in the power supplies. The detector 18 is also insulated. Automatic correction for barometric pressure and patient temperature can also be provided in the monitor 20 in order to produce a direct digital read-out of actual pressure without the need for manual conversion. Such correction would be implemented by a microprocessor which would read in data from a barometric pressure transducer, such as a National Semiconductor LX3701A or LX3801A; decode a manually fed reading of the patient's temperature; perform the frequency counter function to determine the frequency of the variable marker when aligned with the resonant dip (or generate the marker signal with synthesizer techniques); and execute a stored program using this data with pre-determined parameters of the implanted transducer 10 to obtain a digital read-out of intracranial pressure.

Figure 12:
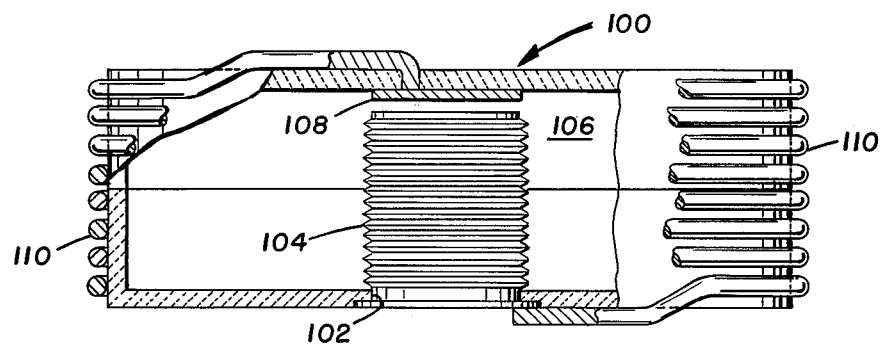
FIG. 12 is an elevation in partial section of a second embodiment of the transducer.

The transducer 10 may be configured otherwise than is described hereinabove. Referring now to FIG. 12, a cylindrical ceramic enclosure 100, which can be formed in essentially the saame manner as the ceramic portion of the transducer 10, is seen to have a central aperture 102 in only one planar face thereof. The aperture 102 has a metal bellows 104 bonded therein with the closed end of the bellows 104 extending into the chamber 106 essentially defined by the ceramic enclosure 100. Opposite the closed end of the bellows 104 on the inner wall of the upper planar face of the enclosure 100 is a flat pad 108 of metal, the pad 108 facing the planar closed end of the bellows 104. An inductance coil 110 is wound about the enclosure 100 in the same manner as has been described relative to the transducer 10, the coil 110 being electrically joined at its respective ends to the bellows 104 and to the metal pad 108. The metal pad 108 and the closed end of the bellows 104 are spaced apart a pre-determined distance in the manner that was previously described relative to the fabrication of the transducer 10. Thus, a circuit is established which consists of the metal pad 108, the bellows 104, and the inductance coil 110, the circuit essentially being a passive "LC", circuit, i.e., a circuit having an inductance and a capacitance, in the manner of the circuit formed by the bellows 28, 30 and the inductance coil 36 of the transducer 10. In the embodiment shown in FIG. 12, one of the bellows has been eliminated, thereby providing a more simple structure. The transducer thus formed would be encased for implantation and utilized essentially in the same fashion as the transducer 10.

Figure 13:
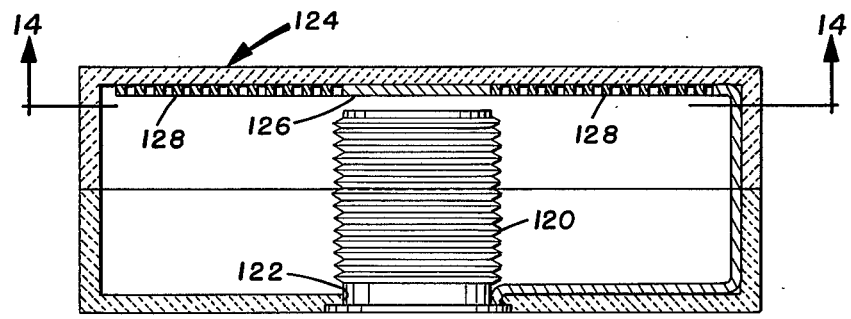
FIG. 13 is an elevation in partial section of a third embodiment of the invention.
Figure 14:
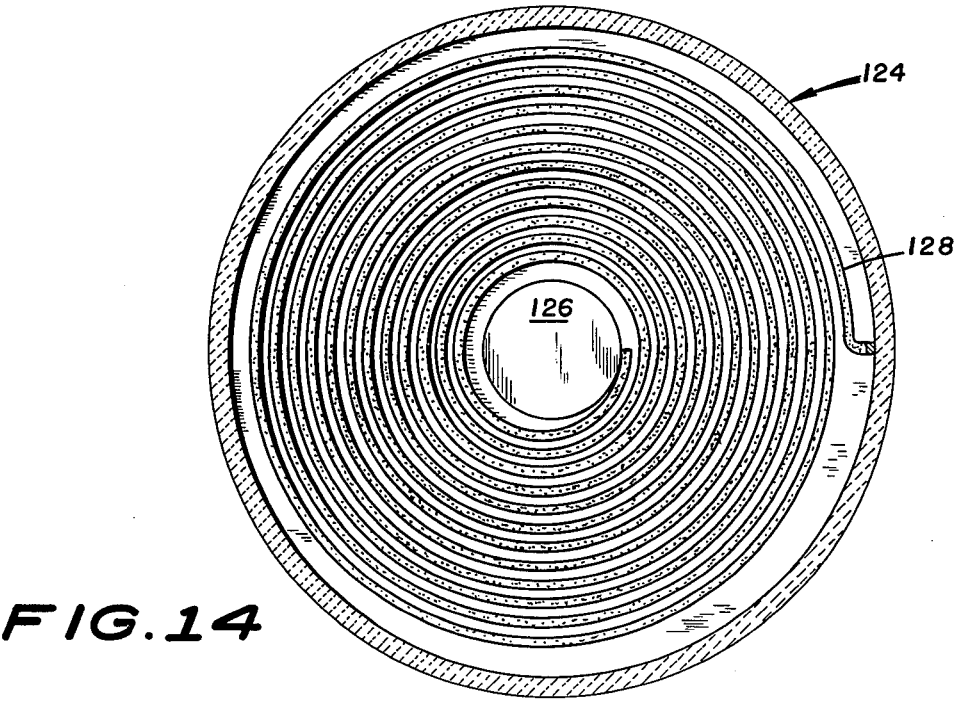
FIG. 14 is a top view in section of the embodiment of FIG. 13.

Referring now to FIGS. 13 and 14, another embodiment of the invention can be seen to utilize only one bellows 120, the bellows 120 being bonded within aperture 122 formed in one planar face of a cylindrical ceramic enclosure 124. The ceramic enclosure 124 is formed in essentially the same manner as is the ceramic portion of the transducer 10 as aforesaid. The opposite interior wall of the upper planar face of the enclosure 124 has a flat pad 126 of metal formed thereon, the pad 126 being spaced from and oppositely facing the closed end of the bellows 120. On the aforesaid interior wall on which the pad 126 is disposed, an inductance coil 128 is formed such as by chemical milling, vacuum deposition, or the like. The coil 128 preferably takes the form of a spiral, electrically connecting to the pad 126 at its inner end and extending along the interior of the enclosure 124 to connect with the bellows 120 at its outer end. The spiral coil 128 can have any number of turns which provides a reasonable Q value to the circuit thus formed by the pad 126, the bellows 120, and the coil 128, the coil 128 being shown with twelve turns as a typical example. The coil 128 is shown as a spiral since this geometric figure provides a continuous electrical path between the turns of the coil. Other geometrical patterns wherein the turns of the coil 128 are electrically continuous therebetween are essentially equivalent and therefore suitable. The inductance of the spiral coil 128 is clearly not as great as a coil of the same number of turns in which all of the coils subtend the same area as is the case with the coils 36 and 110 described hereinabove. However, the ease with which the coil 128 and pad 126 can be formed, coupled with the use of only one bellows 120, causes the structure shown in FIGS. 13 and 14 to be an economically attractive embodiment of the present invention.

Figure 15:
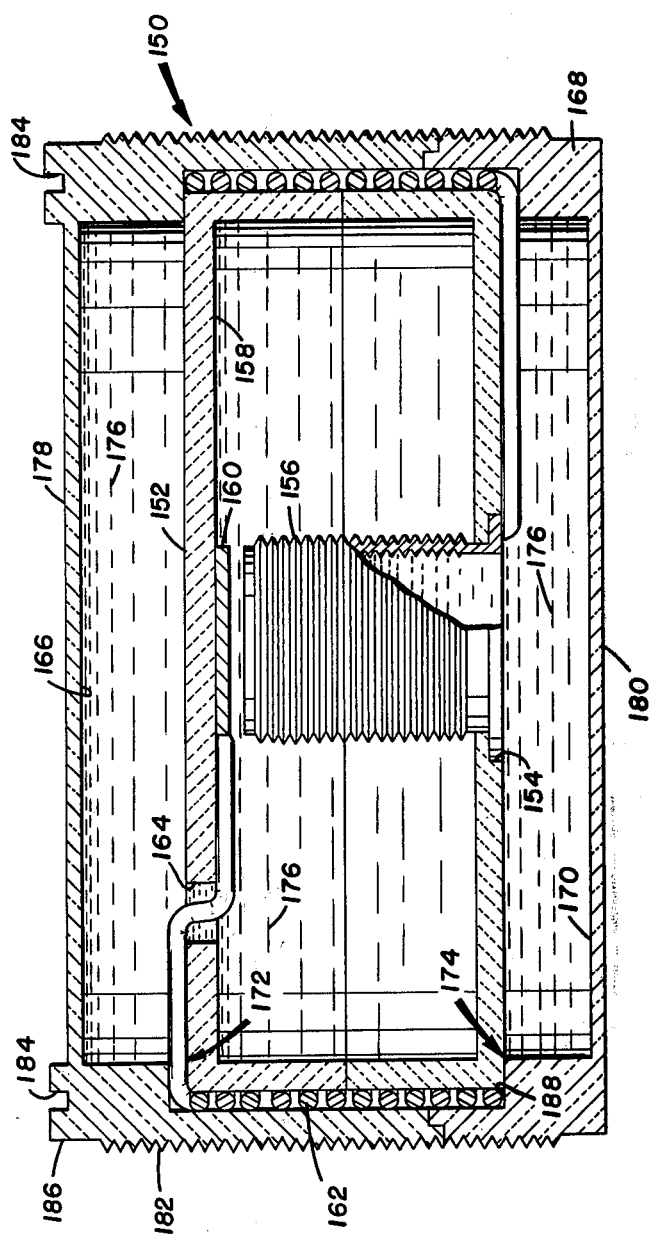
FIG. 15 is an elevation in partial section of a gauge-pressure embodiment of the invention.

The transducer structures described above can all be used with the external detector 18 and monitor 20. These transducer structures measure absolute pressure and are thus subject, as foresaid, to changes in body temperature, barometric pressure, and/or changes in the reference pressure levels within the transducers. Corrections for one or more of these factors are required at times. The embodiment of FIG. 15 provides a transducer structure which measures gauge pressure, or the differential pressure between atmospheric pressure and the intracranial pressure seen by the transducer. Correction need not be made during use of this embodiment of the invention for temperature or barometric pressure. Further, drift of the reference pressure within the transducer of FIG. 15 is also effectively immaterial to its use since only a differential pressure is measured. Referring now to FIG. 15, a transducer 150 is seen to be comprised of a cylindrical ceramic enclosure 152 having a central aperture 154 formed in one planar face thereof. A metal bellows 156 is bonded within the aperture 154 with the closed end of the bellows 156 extending into a chamber 158 essentially defined by the ceramic enclosure 152. A metal pad 160 is formed on the inner wall of the upper planar face of the enclosure 152, the metal pad 160 being spaced from and oppositely facing the closed end of the bellows 156. An inductance coil 162 is wound about the enclosure 152 in the same manner as has been described relative to the transducer 10, the coil 162 being electrically joined at its respective ends to the bellows 156 and to the metal pad 160. The extension of the conductive coil which leads to the metal pad 160 can pass through a vent hole 164, which also has another function, or it can pass through a separate aperture provided solely for that purpose. The metal pad 160 and the closed end of the bellows 156 are spaced apart a pre-determined distance in the manner that was previously described relative to the fabrication of the transducer 10. Thus, a circuit is established which consists of the metal pad 160, the bellows 156, and the inductance coil 162, the circuit essentially being a passive LC circuit.

In effect, the transducer 150 as shown in FIG. 15 is physically similar to that structure shown in FIG. 12. It is to be understood, however, that the essential physical structure shown in FIGS. 13 and 14 could alternatively be substituted for the transducer 150. It is to be understood that the bellows 156 could be disposed to communicate with either of the chambers 166 or 170, but not with both. The vent hold 164 would then communicate the chamber 158 with whichever chamber 166 or 170 which does not communicate with the interior of the bellows 156. An important aspect of the practice of this embodiment of the invention is the provision of the vent hole 164 in the ceramic enclosure 152 which allows communication between the chamber 158 and an outer chamber 166 which surmounts the transducer 150. The transducer structures of FIG. 12 and FIGS. 13 and 14 would be so configured if substituted into this embodiment of the invention. The chamber 166 is defined by the upper portion of a casing 168, the lower portion of the casing 168 defining a lower chamber 170, the chambers 166 and 170 being sealed, such as at 172 and 174, to prevent communication therebetween. A fluid 176, such as silicone oil, is disposed within the chambers 166 and 170. Since the chamber 166 and the chamber 158 of the transducer 150 communicate through the vent hole 164, the fluid 176 fills both chambers 158 and 166. The fluid 176 within the lower chamber 170 also fills the interior of the bellows 156. However, the fluid 176 does not communicate between the chambers 166 and 170.

The casing 168 has upper and lower planar faces 178 and 180, the upper planar face 178 essentially is responsive to atmospheric pressure when implanted beneath the scalp such as shown in FIGS. 1 and 2, the pressure immediately beneath the scalp being the same as or an approximation of atmospheric pressure. The pressure within the chambers 166 and 158 being therefore related to atmospheric pressure. The lower planar face 180 of the casing 168 is brought into contact with the dura as described hereinabove so that the pressure within the lower chamber 170 is related to the intracranial pressure. The pressure within chambers 158 and 166 and the pressure within chamber 170 are transmitted through fluid 176 to cause the closed end of the bellows 156 to assume a position relative to the metal pad 160 which is a function of the difference between the atmospheric pressure and the intracranial pressure. Thus, through use of threads 182 on the outer cylindrical faces of the casing 168, the structure of FIG. 15 can be implanted in the same manner as can the transducer 10, i.e., such as within the threaded collar 58. Since the upper planar face 178 of the casing 168 should be formed with a minimum thickness consistent with structural integrity in order to facilitate pressure transfer across the face, slots 184 are preferably formed in the outer rim 186 of the casing 168 rather than in the planar face 178. A spanner wrench or the like can then be used to rotate the threaded casing 168 within a mounting collar such as the collar 58. The lower planar face 180 is also formed with a minimum thickness in order to facilitate transfer of pressure across the face.

The rim 186 if formed to extend upwardly above the level of the upper planar face 178 in order to prevent pressure-causing impingement of the scalp on the face 178. A perforated shroud (not shown) could also be placed in surmounting spaced relation to the face 178 to prevent actual contact between the face 178 and the scalp.

The structure of FIG. 15 can be externally monitored such as by the external detector 18 and monitor 20 described previously. The signal thus generated would not need either manual or automatic correction for temperature or barometric pressure. More importantly, drift of the reference pressure due to changes in gas volume, such as in the chamber 34 of the transducer 10, which changes can occur for a variety of reasons both related to and unrelated to leakage to or from the chamber 34, need not be considered with the structure of FIG. 15 since "gauge" pressure is measured directly by this embodiment without the need for pressure or temperature corrections.

The enclosure 152 can be formed of ceramic or other refractory material in order to provide structural stiffness. Other suitable materials could include structurally stiff plastics, etc., which are non-toxic and have a low dielectric constant. The enclosure 152 can be fitted into an annular race 188 to maintain said enclosure at a desired location within the casing 168. The chambers 177 and 170 can then be conveniently sealed from each other at one or both of the shoulders of the race 188. Most of the fabrication techniques described above relative to the encased transducer 10, such as epoxy bonding of the casing, can also apply to fabrication of the transducer 150.

As should be apparent from the foregoing, the invention can be practiced other than as specifically described hereinabove without departing from the scope and intent of the invention. In particular, the circuit formed within the transducers could be configured to contain a capacitance across the inductance portion of the circuit. Such a circuit would result from the simple expedient of not providing an electrical connection between the bellows. A circuit so formed would still comprise a resonant circuit having a large Q and which could be monitored in a manner similar to that described hereinabove. Further, only a single bellows could be used in the transducer 10. It is therefore apparent that the invention is to be limited only by the definition provided by the appended claims.

What is claimed is:

1. Apparatus for sensing pressure within a cavity in the body of a living entity, comprising:
   means deformable in response to pressure within the cavity, said means comprising
      a housing formed of non-porous and electrically non-conductive material, the housing defining a chamber,
      a predetermined mass of fluid disposed within the chamber, and,
      pressure responsive means carried on the housing and extending into the chamber, said pressure responsive means being formed of non-porous and elastically compliant material and being deformable by pressure imposed on the apparatus to change the volume occupied by the mass of fluid within the chamber; and
   circuit means for absorbing electromagnetic radiation imposed thereon from externally of the circuit means at frequencies indicative of the deformation of the first-mentioned means.

2. The apparatus of claim 1 and further comprising:
    means housing the first-mentioned means and the circuit means, the housing means being totally implantable within the aforesaid cavity;
    means for imposing electromagnetic radiation on the circuit means within the implanted housing means; and,
    means for detecting the frequency at which the circuit means most efficiently absorbs the imposed electromagnetic radiation.

3. The apparatus of claim 2 and further comprising means for converting the detected frequency to a corresponding pressure reading and for displaying the pressure reading.

4. The apparatus of claim 2 wherein at least portion of the imposing means and the detecting means are disposed on a mounting substrate, the substrate having an aperture therein for receiving discrete tool means for positioning the housing means at a desired location within the aforesaid cavity.

5. The apparatus of claim 1 wherein the fluid comprises nitrogen gas.

6. The apparatus of claim 1 and further comprising at least two electrically conductive surfaces disposed in opposing relation to each other and movable relative to each other in response to deformation of the pressure responsive means, the surfaces forming at least a capacitive portion of the circuit means.

7. The apparatus of claim 6 and further comprising inductive means disposed in proximity to the electrically conductive surfaces, the, inductive means forming an inductive portion of the circuit means.

8. The apparatus of claim 1 wherein the inductive means comprise a coil of electrically conductive material.

9. The apparatus of claim 8 wherein the coil is electrically connected to each of the electrically conductive surfaces to form a resonant circuit.

10. The apparatus of claim 1 wherein the pressure responsive means comprise at least one bellows formed of an electrically conductive material and having a substantially planar end portion extending into the chamber, the apparatus further comprising:
    electrically conductive means disposed within the chamber and having a substantially planar surface opposing the planar end portion of the bellows, said surface and said planar end portion being movable relative to each other in response to deformation of the bellows, the surface of the electrically conductive means and the planar end portion of the bellows forming at least a capacitive portion of the circuit means.

11. The apparatus of claim 10 wherein the electrically conductive means is comprised of a second bellows and the substantially planar surface thereof is an end portion of the second bellows.

12. The apparatus of claim 10 and further comprising a coil of electrically conductive material, the coil being electrically connected to the bellows and to the electrically conductive means, the coil forming an inductive portion of the circuit means.

13. The apparatus of claim 12 wherein the coil is wrapped around the outer portion of the housing means.

14. The apparatus of claim 12 wherein the coil of electrically conductive material comprises a planar helix.

15. The apparatus of claim 1 and further comprising:
    means encapsulating the housing means, the encapsulating means being totally implantable within the aforesaid cavity; and
    a fluid disposed within the encapsulating means between interior walls of said encapsulating means and the housing means.

16. The apparatus of claim 15 and further comprising collar means for mounting the encapsulating means within the aforesaid cavity, the encapsulating means and the collar means having engaging portions formed respectively thereon, the encapsulating means being movable within the collar means to a desired location therein.

17. The apparatus of claim 16 wherein the engaging portions on the encapsulating means and on the collar means comprise mating threads.

18. The apparatus of claim 17 and further comprising slot means in at least the upper portions of the encapsulating means to facilitate rotation of the encapsulating means within the collar means.

19. The apparatus of claim 16 wherein the encapsulating means has a portion thereof which is structurally relatively thin to facilitate transfer of pressure externally imposed on the encapsulating means to the fluid disposed within the encapsulating means and externally of the housing means.

20. The apparatus of claim 1 wherein the housing has an aperture therein used for sealing the mass of fluid within the chamber, the apparatus further comprising means for sealing the aperture to prevent introduction of extraneous gaseous material into the chamber, the last-mentioned means comprising pin means insertable into the aperture, and solder means for joining the pin means to a portion of the exterior surface of the housing.

21. The apparatus of claim 20 wherein the last-mentioned means comprise a collar of metal formed about the periphery of the aperture, the solder means joining to the collar.

22. Apparatus for sensing pressure within a cavity in the body of a living entity, comprising:
    means deformable in respone to pressure within the cavity, said means comprising
        a first housing,
        a second housing disposed within the first housing, thereby to define first and second chambers within said first housing between interior walls of the first housing and exterior walls of the second housing, the second housing defining an interior chamber therewithin and further having an aperture communicating the interior chamber with one of the aforementioned chambers,
        a fluid disposed within the aforesaid chambers, and,
        pressure responsive means carried on the second housing and extending into the interior chamber, the pressure responsive means being deformable by pressure imposed on the apparatus to change the volume occupied by the mass of fluid within the interior chamber; and,
    circuit means for absorbing electromagnetic radiation imposed thereon from externally of the circuit means at frequencies indicative of the deformation of the first-mentioned means.

23. The apparatus of claim 22 and further comprising at least two electrically conductive surfaces disposed in opposing relation to each other and movable relative to each other in response to deformation of the pressure responsive means, the surfaces forming at least a capacitive portion of the circuit means.

24. The apparatus of claim 22 wherein the pressure responsive means comprise at least one bellows formed of electrically conductive material and having a substantially planar end portion extending into the interior chamber, the interior of the bellows communicating with the one of the first or second chamber which does not communicate with the interior chamber through the aforementioned aperture.

25. The apparatus of claim 24 and further comprising:
electrically conductive means disposed within the interior chamber and having a substantially planar surface opposing the planar end portion of the bellows said surface and said planar end portion being movable relative to each other in response to deformation of the bellows.

26. The apparatus of claim 24 and further comprising a coil of electrically conductive material, the coil being electrically connected to the bellows and to the electrically conductive means.

27. The apparatus of claim 26 wherein the coil is wrapped about an outer portion of the second housing means.

28. The apparatus of claim 22 and further comprising inductive means disposed in proximity to the electrically conductive surfaces, the inductive means forming an inductive portion of the circuit means.

29. The apparatus of claim 28 wherein the inductive means comprise a coil of electrically conductive material.

30. The apparatus of claim 28 wherein the coil is electrically connected to each of the electrically conductivesurfaces to form a resonant circuit.

31. The apparatus of claim 22 wherein the fluid comprises silcone liquid.

32. The apparatus of claim 22 and further comprising:
means housing the first-mentioned means and the circuit means, the housing means being totally implantable within the aforesaid cavity;
means for imposing electromagnetic radiation on the circuit means within the implanted housing means; and,
means for detecting the frequency at which the circuit means most efficiently absorbs the imposed electromagnetic radiation.

33. The apparatus of claim 22 and further comprising:
means for converting the detected frequency to a corresponding pressure reading and for displaying the pressure reading.

34. Apparatus for sensing pressure within the cranial cavity of a living entity, comprising:
a first housing;
a second housing disposed within the first housing, thereby to define first and second chambers within said first housing between interior walls of the first housing and exterior walls of the second housing, the second housing defining an interior chamber therewithin and further having an aperture communicating the interior chamber with one of the aforementioned chambers;
a fluid disposed within the interior chambers and within the first and second chambers;
sealing means for sealing the first chamber from communication with the second chamber; and,
pressure responsive means carried on the second housing and extending into the interior chamber, the pressure responsive means being deformable by pressure imposed on the apparatus to reduce the mass of fluid within the interior chamber.

35. Apparatus for sensing pressure within the cranial cavity of a living entity, comprising:
a housing formed of non-porous and electrically non-conductive material, the housing defining a chamber;
a predetermined mass of fluid disposed within the chamber;
pressure responsive means carried on the housing and extending into the chamber, said pressure responsive means being formed of non-porous and elastically compliant material and being deformable by pressure imposed on the apparatus to reduce the volume of the mass of fluid within the chamber; and,
circuit means for absorbing electromagnetic radiation imposed thereon from externally of the apparatus at frequencies indicative of the deformation of the pressure responsive means, the circuit means including at least two electrically conductive surfaces at least one of which is carried on the pressure responsive means, the conductive surfaces being disposed in opposing relation to each other and movable relative to each other in response to deformation of the pressure responsive means, the surfaces forming at least a capacitive portion of the circuit means, the circuit means also including inductive means disposed in proximity to the electrically conductive surfaces, the inductive means forming an inductive portion of the circuit means, the inductive means being electrically connected to each of the electrically conductive surfaces to form a resonant circuit.

* * * * *